United States Patent [19]
Hariri et al.

[11] Patent Number: 4,875,482
[45] Date of Patent: Oct. 24, 1989

[54] FLEXIBLE GRASPING DEVICE

[75] Inventors: Robert J. Hariri; Jamshid B. G. Ghajar; Fathali Ghahremani-Ghadjar, all of New York, N.Y.

[73] Assignee: Neurodynamics, Inc., New York, N.Y.

[21] Appl. No.: 209,434

[22] Filed: Jun. 21, 1988

[51] Int. Cl.⁴ .............................. A61B 17/42
[52] U.S. Cl. .................................... 128/352
[58] Field of Search ................. 128/352, 353, 361

[56] References Cited

U.S. PATENT DOCUMENTS

| 13,453 | 8/1855 | Buffum . | |
| 497,720 | 5/1893 | Jones . | |
| 713,166 | 11/1902 | St. Cyr . | |
| 1,448,739 | 3/1923 | Godfrey | 128/352 |
| 1,690,942 | 11/1928 | Odell . | |
| 1,782,814 | 11/1930 | Froehlich . | |
| 2,194,989 | 3/1940 | Torpin | 128/361 |
| 2,227,673 | 1/1941 | Price | 128/352 |
| 2,792,838 | 5/1957 | Guerriero | 128/361 |
| 3,592,198 | 7/1971 | Evans | 128/352 |
| 3,765,408 | 10/1973 | Kawai | 128/352 |
| 3,794,044 | 2/1974 | Vennard et al. | 128/352 |
| 4,018,230 | 4/1977 | Ochiai et al. | 128/344 |
| 4,136,679 | 1/1979 | Martinez et al. | 128/1 R |
| 4,512,347 | 4/1985 | Uddenberg | 128/352 |
| 4,597,391 | 7/1986 | Janko | 128/361 |
| 4,602,623 | 7/1986 | Cherkassky | 128/323 |

FOREIGN PATENT DOCUMENTS

| 2233840 | 1/1974 | Fed. Rep. of Germany | 128/361 |
| 2739589 | 3/1979 | Fed. Rep. of Germany | 128/361 |
| 2925386 | 1/1981 | Fed. Rep. of Germany | 128/361 |

Primary Examiner—Michael H. Thaler
Attorney, Agent, or Firm—Pennie & Edmonds

[57] ABSTRACT

A device is disclosed comprising a stretchable cylindrical net-like structure and at least one guide ring for partial placement over a fetus. The cylindrical net-like structure is formed such that as force is applied along its longitudinal axis, the length of the cylindrical structure is increased while the diameter of such cylindrical structure is decreased. The guide ring is expandable for passage therethrough of the fetal head and has an at rest diameter between that of the fetal neck and the fetal head.

25 Claims, 5 Drawing Sheets

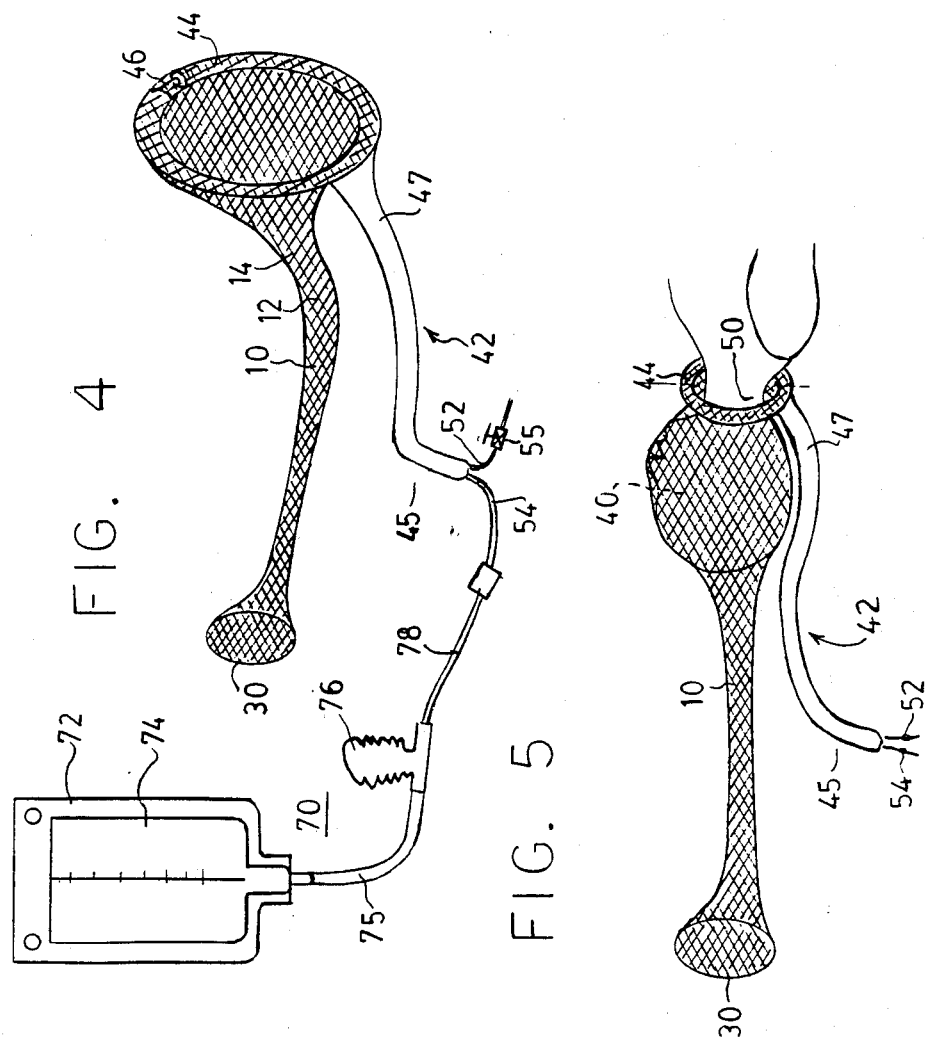

FLEXIBLE GRASPING DEVICE

TECHNICAL FIELD

The present invention relates generally to a flexible grasping device and more particularly to a stretchable net having an opening for receiving a fetal head and aiding in the passage of the fetus through the birth canal.

BACKGROUND OF THE INVENTION

Approximately thirty percent of all vaginal birth deliveries are complicated by some degree of cephalopelvic disproportion, or in other terms, the inability or difficulty of the maternal birth canal to accommodate the size of the fetal head. The fetal head, of course, typically represents the largest diameter of any section of a fetus and thus once the fetal head has protruded, completion of the delivery is simplified. In cases of extreme disproportion, the fetal head cannot engage and transabdominal delivery, i.e., Caesarean section, is necessary. However, in a number of cases the degree of disproportion is minimal and the fetal head will descend into the birth canal only to become trapped at the level of the maternal pubic ramus, unable to pass through due to the sharp angle which must be negotiated. In these cases, metal delivery forceps are employed to grasp the fetal head and either guide it or apply traction to it, to facilitate passage through the birth canal.

Such forceps are well known in medical literature as potentially dangerous to the well-being of the fetus and the mother. One of the primary disadvantages of forceps arises from the intense and locally concentrated pressures that known forceps apply to a fetal head. Such pressures are generally only applied to opposite sides of the fetal head and have resulted in permanent brain injury, bone and soft tissue injury (including enucleation, avulsion of the ear, facial nerve palsy, fracture of the mandible, fracture of the skull, etc.). In addition, the use of known forceps has also resulted in injury to the mother, including cervical and vaginal lacerations resulting in significant hemorrhage and requiring immediate attention by an obstetrician having considerable experience.

Although forceps for aiding in the delivery of a fetus have been in use for hundreds of years and hundreds of types of forceps have been produced since the introduction of the original Chamberlain forceps, all such forceps are based on the same mechanical principle, namely that of the tongs. More specifically, such known forceps comprise long and rigid shafts terminating in a blade-like member for controlling the fetal head and pivoted together such that application of force to the handles of such forceps results in the blade-like members moving towards or away from each other, but always in a single plane.

An additional deficiency of known forceps relates to an inherent difficulty or inability to apply purely tractive forces to a fetal head due to relative orientation of the fetal head, the forceps, the birth canal and the maternal pelvic bone structure. These problems and limitations have made it necessary to seek alternative methods to aid in fetal head delivery.

Illustrative of such alternate methods include the use of vacuum suction devices in which a cap-like device is placed on the fetal head, suction is applied and the fetus is withdrawn through the birth canal. For example, U.S. Pat. No. 3,765,408 to Kawai discloses a soft elastic vacuum cap having a plurality of recessed spaced apart orifices within an inner surface of the cap and close to an edge of the cap. Such orifices are commonly connected to a suction tube. In practice, the cup is inserted into the vagina and negotiated so as to contact the fetal head whereupon suction is applied and the fetus withdrawn.

U.S. Pat. No. 3,794,044 discloses delivery forceps comprising a plurality of retractable flexible fingers which are contoured generally to the shape of the fetal head. The device, with the fingers retracted into a hollow member, is inserted into the vagina until it abuts the fetal head, at which point the retracted fingers are extended and surround the fetal head. A noose portion attached to the finger tips is tightened and the fetus withdrawn. A thin membrane may be provided to interconnect the fingers and suction may be applied to further secure the fingers and membrane to the head.

Unfortunately, difficulty has been encountered in positioning such vacuum suction devices in the birth canal so as to adequately contact the fetal head. Furthermore, such devices tend to be large, cumbersome, bulky, complex and expensive. Additionally, although apparently and potentially an improvement over forceps, vacuum suction devices tend to suck the fetal head into the cap-like suction member, especially since the fetal head is relatively pliable, resulting in permanent scarring and other injury. More specifically, use of vacuum extraction on the fetus is believed to be a cause of trauma to the fetal scalp, fetal subgaleal hematosis, fetal scalp lacerations and skin necrosis. Fetal intracranial and intraocular hemorrhages have also been reported as a result of vacuum extraction, as has damage to the soft vaginal tissue of the mother. Extreme care must also be taken not to injure the fetus with any finger-like projections employed by the vacuum suction device.

U.S. Pat. No. 4,602,623 to Cherkassky discloses an apparatus comprising one or more sheets of material to be placed between the fetus and a wall of the birth canal. Such sheets have low coefficients of friction such that friction between the fetus and the canal wall is reduced during delivery.

U.S. Patent Nos. 13,453 to Buffum, 497,720 to Jones, 1,690,942 to Odell, 1,782,814 to Froehlich, 2,227,673 to Price and 2,792,838 to Guerriero generally disclose devices which may be placed around a fetal head often with the aid of finger-like members, tightened, and subsequently withdrawn.

Further known devices are disclosed in U.S. Pat. Nos. 4,018,230 to Ochiai et al. (an inflatable cervical dilator), 4,136,679 to Martinez et al. (a pistol-gripped spatula terminating in a solid scoop), 4,512,347 to Uddenberg (suction device comprising a rigid cap-like member), 3,592,198 to Evans (flexible cap-like member placed over fetal head and subsequently hardened through use of a thermosensitive compound to retain the fetal head).

U.S. Pat. Nos. 713,166 to St. Cyr and 4,597,391 to Janko disclose nets for delivery of a fetus, such nets having an end manually expandable for placement over a fetal head. However, the St. Cyr device requires two long rigid finger-like members for proper placement of the longitudinally slit net around a fetal head. The Janko device also requires a plurality of structural ribs to hold the general pattern of the longitudinally slit net. In each of these devices, the device as inserted is in the form of an elongated tube-like member and placed next to the fetal head. Only at this point may the device be opened and unfolded in a fan-like manner to surround the fetal head. During insertion of the device which is in the form of a tube-like member as well as during the subsequent unfolding process, the fetal head is continually prone to injury from the tip ends of the finger-like members. Additionally, once the net is unfolded, the finger-like projections must somehow mate and be joined to each other. Furthermore, the mechanical procedure of opening and unfolding the device, surrounding the fetal head and joining the end finger-like members exposes not only the fetus but also the mother to unnecessary and potentially harmful frictional forces. Extreme care must be taken so as to not injure the fetus with such finger-like members.

Due to the shortcomings of known devices described above, failure of medical personnel to accept such known devices and methods, and a decreased amount of training taught by medical institutions in the use of forceps and the resulting unfamiliarity with forceps of today's medical personnel, Caesarean section deliveries have become relatively common. Unfortunately, such Caesarean section deliveries are not without risks and complications, as is well documented in the medical field. Furthermore, there has been recent increased concern with the liberty with which Caesarean section deliveries are performed. Additionally, if a Caesarean section delivery is performed on a first birth, subsequent births are also likely to be by Caesarean section.

SUMMARY OF THE INVENTION

The present invention relates to an obstetric device for the tractive delivery of a fetus comprising an elongated cylindrical net-like structure which has a plurality of interconnected threads defining a plurality of openings and a guide means which is attached at a first end of the cylindrical net-like structure. The guide means is inserted through a birth canal preferably to the level of the fornicies and defines an opening of the net-like structure for receiving a fetal head and thereby prevents displacement of the net-like structure by the passage of the fetal head through the birth canal. Advantageously, the first end of the elongated net-like structure applies an increased grasping force to a fetal head inserted therein as tractive force is applied to a second end of the elongated cylindrical net-like structure.

The plurality of interconnected threads preferably defines a flexible fabric and the guide means preferably comprises a guide ring. The guide ring may be provided with handle means. Further, the plurality of threads of the net-like structure may be knitted to define a mesh. The threads may take on the form of individual fibers knitted to define a mesh or, alternatively, may take on the form of braided strands of fibers knitted to define a mesh.

The guide ring may comprise an elongated member having a first end and a second end formed into a circular structure such that the first end is overlapping and adjacent to the second end, wherein the guide ring is constrictable or expandable by the application of force to constrict or enlarge the ring. Alternatively, the guide means may comprise an inflatable annular ring. The inflatable guide ring may comprise an expandable ring having a diameter which is expandable by introduction of a pressurized fluid so as to accommodate the fetal head. The inflatable ring may be pneumatically or hydraulically expandable. A handle means may also be attached to the guide ring.

Means may be included for providing directional control and angular positioning of the fetal head in the birth canal to facilitate delivery. Such means for providing directional control and angular positioning of the fetal head may, for example, comprise a second guide means attached at a second end of the cylindrical net-like structure.

A drawstring may be attached to the first end of the net-like structure for reducing the diameter of the net-like structure around the fetal neck, thus insuring that the net-like structure will remain on the fetal head as tractive force is applied.

The present invention also relates to an obstetric device for the tractive delivery of a fetus comprising a cylindrical flexible net having a first opening at one end, such first opening adapted for receiving at least a portion of a fetus within a birth canal during delivery of such fetus. In such an embodiment, the cylindrical net extends outwards from the birth canal and terminates at a second end, wherein tractive force applied to the second end tends to elongate the cylindrical flexible net to decrease the diameter of the cylindrical flexible net, thereby applying uniformly increasing forces to the fetal portion for tractive delivery of the fetus. Such an obstetric device may also include means for providing directional control and angular positioning of the fetal portion in the birth canal.

Preferably, the obstetric device includes a first guide means attached to the first end of the cylindrical flexible net. The first guide means advantageously maintains a predetermined diameter of the first opening and is expandable from the predetermined diameter to a larger diameter to facilitate passage therethrough of the fetal portion. The first guide means may comprise a guide ring. Handle means may be attached to the guide ring. The guide ring may be inflatable by introducing fluid into the guide ring, thereby expanding the diameter of the ring in order to pass the ring over a fetal head. Alternatively, the guide ring may be mechanically expandable. A drawstring may also be attached to the first end of the cylindrical flexible net for reducing a diameter of the first end of the net around the fetal neck. Additionally, a second guide means may be attached to the second end of the cylindrical flexible net. Such a second guide means may be a ring which is easily grasped and which facilitates tractive delivery of the fetus. Additionally, the second guide means may provide directional control and angular positioning of the portion of the fetus received by the first opening of the net.

The cylindrical flexible net preferably comprises threads knitted to define a mesh. Such threads, for example, may be individual strands of fibers or braided strands of fibers.

The present invention also relates to an obstetric device for the tractive delivery of a fetus comprising an elongated, cylindrical flexible net-like structure having a plurality of interconnected threads which defines a plurality of openings, a first circular ring formed of a resilient member, such ring located at a first end of the net-like structure to define an opening for receiving a fetal head, wherein the ring is constrictable by the application of force to a smaller diameter for insertion into a birth canal and expandable by the application of force to a larger diameter to allow the fetal head to pass therethrough for positioning of the ring past the fetal head, and a second circular ring attached to a second end of the net-like structure for providing directional control and angular positioning of the fetal head in the birth canal, wherein a tractive force applied to the second end of the structure tends to elongate the net-like structure, thereby applying uniformly increasing forces to the fetal head for tractive delivery of the fetus.

BRIEF DESCRIPTION OF THE DRAWINGS

Preferred embodiments of the invention are described hereinbelow with reference to the drawing figures in which similar elements are labelled similarly and wherein:

FIG. 4 is a perspective view of a second embodiment of the invention in expanded form and including an inflatable guide ring and an inflating apparatus;

FIG. 5 is a perspective view of the apparatus of FIG. 4 enclosed around a fetal head;

DETAILED DESCRIPTION OF THE PREFERRED EMBODIMENTS

Figure 1:
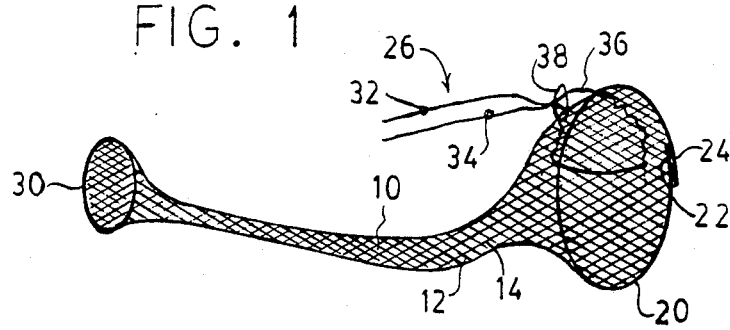
FIG. 1 is a perspective view of a first embodiment of the invention in expanded form and including a drawstring.

Referring initially to FIG. 1, there is illustrated a device for receiving a fetal head and aiding in the passage of a fetus through the birth canal. The device comprises a tubular cylindrical net-like structure 10, first guide ring 20 and second guide ring 30.

Tubular cylindrical net-like structure 10 is a biocompatable material stretchable in both a machine direction and a cross-machine direction. Preferably, the tubular shape of tubular cylindrical net-like structure 10 exhibits a decrease in diameter as it is stretched along its longitudinal axis.

More specifically, tubular cylindrical net-like structure 10 is preferably a knitted material having thread members 12 defining openings 14. As the material is stretched in both a machine direction and a cross-machine direction, thread members 12 elongate, thereby enlarging openings 14. Thus, tubular cylindrical net-like structure 10 easily conforms to the shape of any member around which it is appropriately stretched.

Tubular cylindrical net-like structure 10 is preferably continuous and is formed from suitably knit or woven threads which are compatible with human tissue so as to minimize the danger presented by the introduction of foreign materials into a body, and in particular, to a human fetus and the mother. Suitable materials include nylon, Dacron available from E.I. Du Pont Denemours and Company of Wilmington, Del. and Vicryl available from Ethicon, Inc., Somerville, N.J., a wholly owned subsidiary of Johnson & Johnson. A preferable material and form thereof is a knitted nylon mesh which is biocompatible, easily sterilized, inexpensive, does not require secondary lubricants and has a long shelf life. The knitted nylon mesh is preferably a net-like structure wherein individual fibers are knitted to form the net. However, individual fibers may be braided together to form a braided thread which is then knit to form the net for use with the present invention. Although knitted material is generally preferable, non-knitted material may be acceptable if it is sufficiently stretchable.

The above-identified materials which are suitable for the net-like structure are commercially available and it will be appreciated that a tubular sock-like structure having a suitable length and diameter may be directly knit from fibers or from braided fibers. Alternatively, planar sheets of suitable material may be sewn or otherwise attached so as to form a cylindrical structure These suitable materials are sufficiently inexpensive so as to permit economical disposable use.

First guide ring 20 maintains tubular cylindrical net-like structure 10 in an open position at one end in order to facilitate insertion of the fetal head. First guide ring 20 is depicted in FIG. 1 in an open expanded form for placement over a fetal head. First guide ring 20 has a diameter at rest (See FIG. 2) such that placement of the ring around a fetal neck will not result in injury to the fetus and will aid in maintaining the net around the fetal head as traction is applied In other words, the ring will have a minimum at-rest, non-expanded diameter slightly larger than the diameter of the fetal neck. The maximum at-rest, non-expanded diameter of the ring will be slightly less than the diameter of the fetal head. Thus, the at-rest, non-expanded diameter of first guide ring 20 is within the range between fetal neck diameter and fetal head diameter.

First guide ring 20 is adapted to be expandable such that it may be enlarged, introduced over a fetal head, moved in relation to the fetus towards a fetal neck and then decreased in diameter so as to form a collar-like member which may be removed by re-expanding the ring. First guide ring 20 is constructed from any suitable material which is compatible with human tissue so as to minimize the danger presented by the introduction of foreign materials into a body, and in particular to a fetus and the mother. Furthermore, the material must be sufficiently resilient such that it is capable of being stretched open by hand to a size sufficient to safely accommodate a fetal head. Once stretched to such a size and released, the material must return to its original shape and size.

A suitable guide ring has been formed from a single stainless steel rod member bent into a partially overlapping circular ring and covered with a latex coating The ring is split with opposite ends 22,24 overlapping each other by an amount determined by the diameter of the ring. The guide ring may also be constructed from other suitable material such as an acrylic or a teflon material. Alternatively, a guide ring may take the form of a latex coated small diameter coil spring whose central axis is circular in shape, or an inflatable member (See FIG. 4) to facilitate insertion into the birth canal. An inflatable guide ring comprising a tubular hollow member is preferably inflatable principally along the length of the tubular member as opposed to the diameter of the member, thus being inflatable to provide a ring having a sufficient diameter to accommodate a fetal head.

A drawstring 26, although not necessary for proper operation of the invention, may be provided proximate to guide ring 20 to further insure that the net is maintained around the fetal head as traction is applied. Drawstring 26 comprises a lock ring 38 and a string having a center portion 36 and two end portions 32,34 which pass through lock ring 38. Lock ring 38 is preferably a closed loop structure attached to net 10 and may be constructed from the same material as string portions 32,34 and 36. String portion 36 is preferably at least partially woven into net 10. String portion 36 may be placed a short distance away from guide ring 20 as depicted in FIG. 1 or, alternatively, may be placed adjacent to guide ring 20.

Second guide ring 30, although not necessary for proper operation of the invention, is preferably provided for directional control of the fetal head and also as an alternative guide ring for insertion of a fetal head of different size.

More specifically, as force is exerted on guide ring 30 by appropriate medical personnel in a direction directly away from guide ring 20, such force will be evenly transmitted along cylindrical net-like structure 10 causing it to collapse around the head of the fetus. It will be appreciated that application of force to guide ring 30 may result in transmission of a non-uniform force to the fetal head, depending on the relative orientation of guide ring 30 and the fetal head. Such non-uniform force may advantageously be employed for selective directional control and angular positioning of the fetal head.

In addition to serving as a device for grasping and aiding in directional control, second guide ring 30 serves as an alternative guide ring for the insertion of a fetal head. Preferably, first guide ring 20 and second guide ring 30 are of different sizes and configurations so as to accommodate fetal heads of different size and to facilitate delivery of difficult births.

Figure 2:
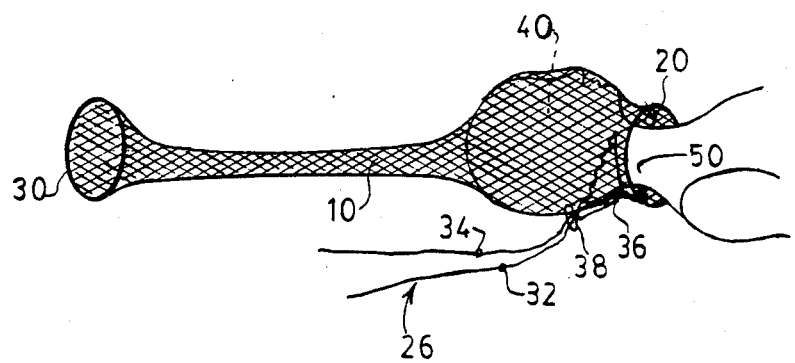
FIG. 2 is a perspective view of the apparatus of FIG. 1 enclosed around fetal head.

Referring now to FIG. 2, there is depicted the device of FIG. 1 enclosed around fetal head 40. Tubular cylindrical net-like structure 10 encloses fetal head 40 and terminates at first guide ring 20. First guide ring 20 is depicted in its at-rest position and has an at-rest diameter which is between the diameter of fetal neck 50 and the diameter of fetal head 40. Drawstring 26 is depicted in a partially drawn manner, thus reducing the possibility of slippage of the net-like structure over the fetal head.

Figure 3:
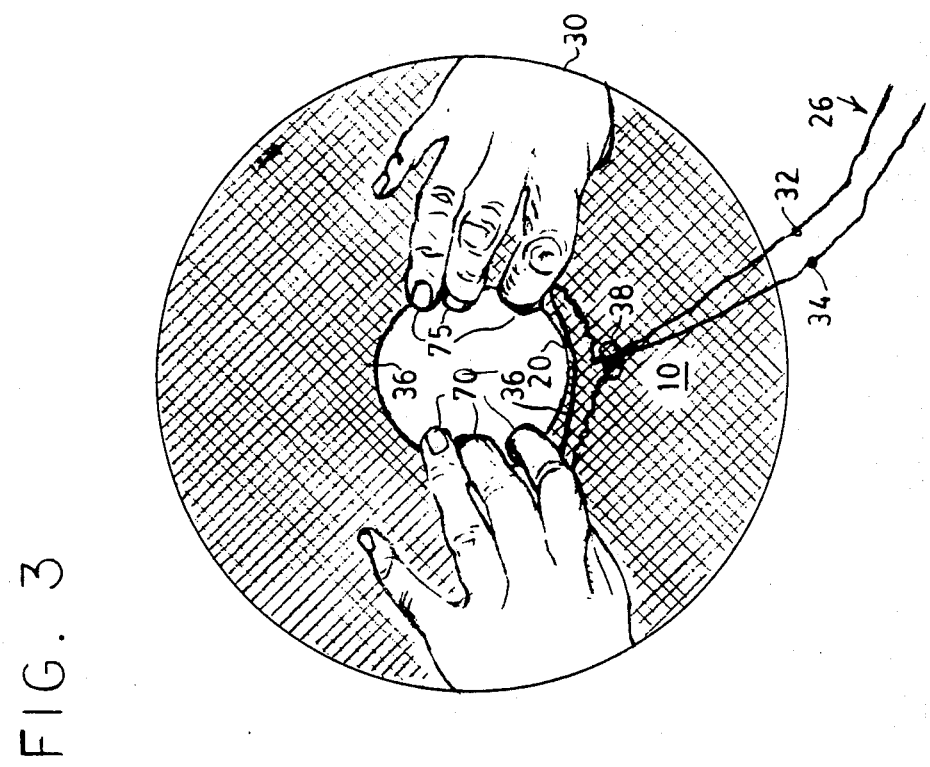
FIG. 3 is a view along a central axis of the apparatus of FIG. 1.

FIG. 3 depicts the invention prepared to receive fetal head. First guide ring 20 is grasped by fingers 0,75 and expanded as necessary in order to accommodate the fetal head (not shown). Once the fetal head has entered and passed through first guide ring 20, the guide ring may be released and its at-rest position maintained around the fetal neck at a diameter between that of the fetal neck and the fetal head. Drawstring 26 may then be drawn thereby reducing the diameter of a portion of the net-like structure to slightly greater than the diameter of the fetal neck.

FIG. 4 depicts a further embodiment of the invention in expanded form which includes an introducer 42 having an inflatable guide ring and an inflating apparatus 70. More specifically, this device comprises net-like structure 10, guide ring 30 and an introducer 42. Introducer 42 comprises an inflatable guide ring 44, a longitudinal section 47 and a pistol grip 45.

Introducer 42 is provided with tubular member 54 for inflating the inflatable ring and tubular member 52 for deflating the inflatable ring. Tubular member 54 is connected to a manual pump 76 by way of piping 78. Manual pump 76 is connected to a saline solution supply 74 by way of piping 75. Saline solution supply 74 is housed in housing 72. In an alternative embodiment, a pressurized air supply and air pressure control valve may be connected to tubular member 54 to control the inflation of inflatable ring 44. Tubular member 52 is connected to a valve means 55. Additionally, a vacuum suction device (not shown) may be connected to valve 55 to facilitate deflation of the inflatable ring 44. In an alternative embodiment, introducer 42 may house the apparatus necessary for mechanically operating the guide ring.

The guide ring may be made of a semi-flexible ring which can be inflated and expanded by exertion of an internal hydraulic or pneumatic force by use of air or a safe fluid such as saline solution, as shown in FIG. 4. The device is inflated after insertion. Once the head of the fetus is in the net, the guide ring can be collapsed around the neck of the fetus thereby permitting appropriate medical personnel to apply necessary tractive force to withdraw the fetus In an alternative embodiment (not shown), guide ring 44 may be made of a pliable impervious material having imbedded fibers and shaped like a hollow tube which can be inflated along the length of the tube hydraulically with a saline solution by way of a pump or pneumatically with pressurized air to a rigid and fixed diameter, thereby allowing the cervix to dilate as well as expanding the entrance of the net to permit the fetal head to enter the net. The rigidity of the guide ring can be maintained by controlling the pressure of the fluid used to expand the tube. In this embodiment, inflation of the ring comprising a hollow tube principally results in elongation of the tube as opposed to an increase in the diameter of the tube, thereby enlarging the diameter of the ring to accommodate a fetal head.

Preferably, introducer 42 aids medical personnel in passing and positioning the guide ring through and in the birth canal to, for example, the fornicies. Additionally, introducer 42 permits the passage of the fluid to the guide ring. The introducer is preferably constructed from any suitable material such as vinyl. Advantageously, the material is sufficiently flexible such that introduction of pressurized fluid into the introducer will add rigidity to the handle as well as inflate and expand the guide ring. Once the head of the fetus is in the net-like structure, the introducer may be depressurized or partially depressurized by way of the valve means and occupy little space in the birth canal.

FIG. 5 depicts the device of FIG. 4 enclosed around a fetal head. Tubular cylindrical net-like structure 10 encloses fetal head 40 and terminates at inflatable guide ring 44. Inflatable guide ring 44 is depicted in its deflated position having an at-rest diameter which is between the diameter of fetal neck 50 and the diameter of fetal head 40. Advantageously, introducer 42 is provided with a longitudinal section 47 which is curved so as to approximately conform to the shape of the fetal head, thus facilitating withdrawal of the fetus and/or insertion of the introducer.

Figure 6:
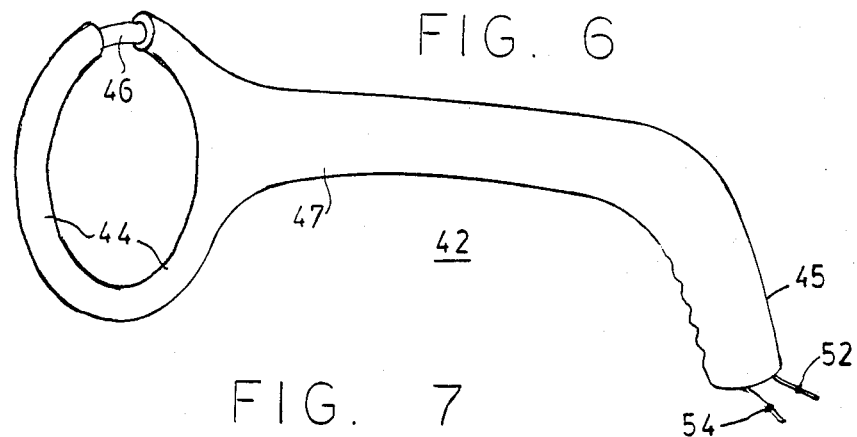
FIG. 6 is a perspective view of the inflatable guide ring and introducer of FIG. 4.
Figure 7:
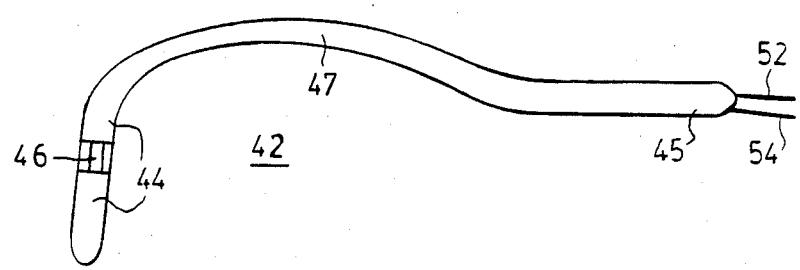
FIG. 7 is a side view of the apparatus of FIG. 6.

FIG. 6 depicts a side view of introducer 42 of FIG. 4 comprising inflatable guide ring 44, longitudinal section 47, pistol grip 45 and curved member 46. FIG. 7 depicts a top view of introducer 42, showing a curvature in section 47 for conforming to the shape of the fetal head.

Figure 8:
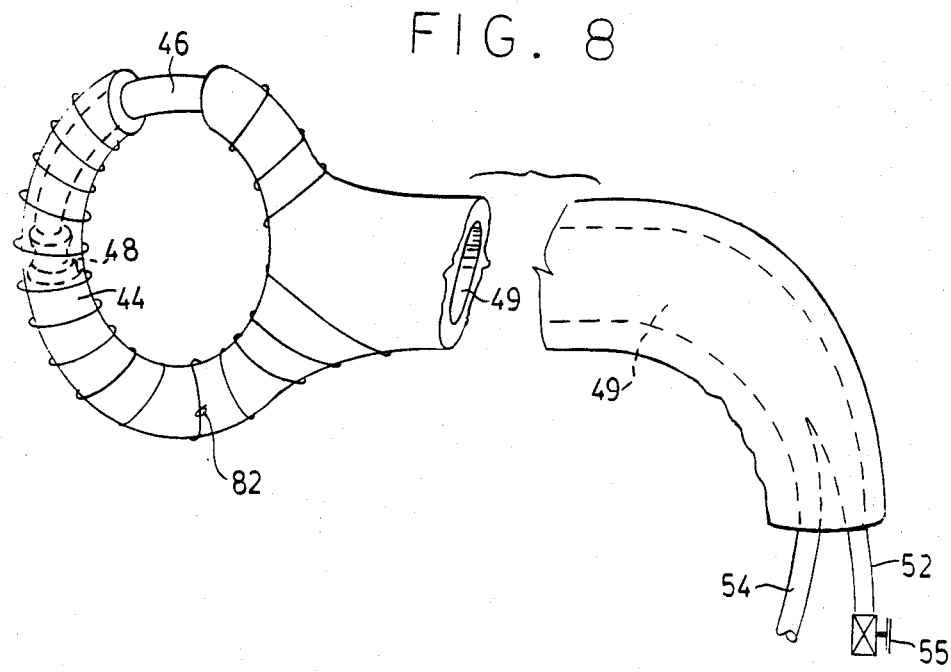
FIG. 8 is a detailed view of the apparatus of FIG. 6.

FIG. 8 depicts a portion of introducer 42 in greater detail. Seal means 48 is provided and is firmly attached to one end of curved member 46 for sealable slidable contact with the inside surface of a section of inflatable ring 44. As will be appreciated inflation of ring 44 is accomplished by introducing fluid into tubular member 54 while maintaining valve 55 in a closed position. The introduced fluid travels through tubular member 54, into channel 49 towards ring 44, thereby causing seal means 48 to slide on the inside surface of ring 44, resulting in enlarging inflatable ring 44. In an alternative embodiment, inflatable ring 44 comprises a hollow inflatable annular ring which increases in diameter as its internal pressure is increased. In this embodiment, the annular ring is constructed from material having suitable flexibility such that it is adequately inflatable and sufficiently rigid when inflated to maintain the net in an open position within the birth canal to accept the fetal head.

A portion 82 of net-like structure 10 is also depicted in FIG. 8 and is attached to inflatable ring 44. Deflation is accomplished by opening valve 55 thereby causing fluid within ring 44 and channel 49 to exit the introducer. If necessary, a vacuum suction device may be connected to valve 55 to facilitate deflation of inflatable ring 44. In an alternative embodiment, a single tubular member is connected to channel 49 and exits introducer 42. In such an embodiment, a T- or Y-type fitting may be provided external to the introducer for connection to the single tubular member exiting introducer 42, the inflating means and the valve means.

Figure 9:
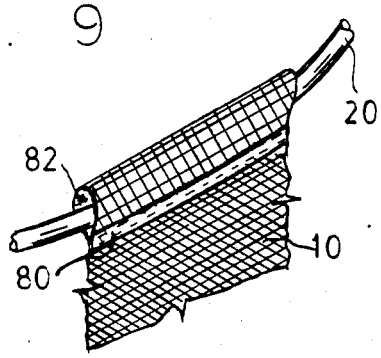
FIG. 9 is a view of an edge of the apparatus where a net is attached to a circular ring.

FIG. 9 depicts the first guide ring 20 and the manner of attachment of tubular cylindrical net-like structure 10 in detail. A seam section 80 is formed by passing a short section 82 of tubular cylindrical net-like structure 10 through guide ring 20 and folding such short section around guide ring 20 back onto itself. Any appropriate fastening means such as stitches or glue having a low level of toxicity may be employed to bind the short section of tubular cylindrical net-like structure. Advantageously, guide ring 20 is free to rotate within the seam formed by the end of tubular cylindrical net-like structure 10 so that guide ring 20 may be expanded in order to accommodate the fetal head. Drawstring circular portion 36 of FIG. 1 may be passed through a cavity 82 adjacent to guide ring 20. In an alternative embodiment, the guide ring of FIG. 9 can take the form of an inflatable guide ring such as that disclosed in FIG. 4.

Figure 10:
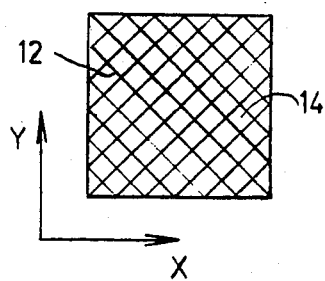
FIG. 10 is a planar view of a representative section of the tubular cylindrical net-like structure of the present invention in a relaxed state.
Figure 11:
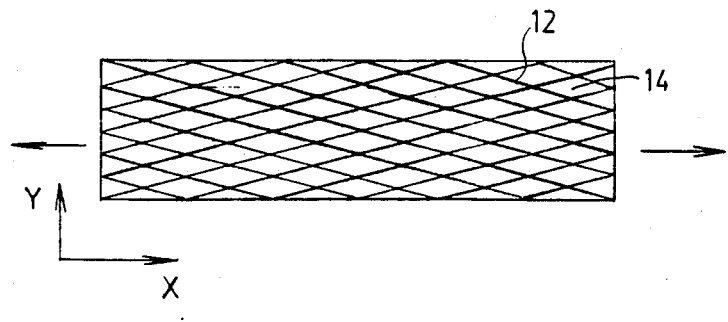
FIG. 11 is a planar view of a representative section of the tubular cylindrical net-like structure of the present invention in a longitudinally stretched state.

FIGS. 10 and 11 depict in detail the structure of the material forming tubular cylindrical net-like structure 10 in both an at-rest position (FIG. 10) and in a unidirectionally expanded position (FIG. 11). More specifically, FIG. 10 depicts the knit, or weave, of tubular cylindrical net-like structure 10 having thread members 12 defining openings 14. Although the at-rest cylindrical net-like structure is depicted in FIG. 10 as having square openings 14, elongated diamond-shaped openings may be provided, as may other shaped openings. It will be appreciated that by modifying the size and/or shape of openings 14, various characteristics relating to degree of stretch, direction of stretch, strength and the like may be obtained.

FIG. 11 depicts the cylindrical net-like structure of FIG. 10 stretched in a unidirectionally expanded configuration. As can be seen, stretching the structure depicted in FIG. 10 along an x-direction increases the length of each opening in the x-direction and decreases the length of each such opening in the y-direction. It will be appreciated that such a decrease in the y-direction increases the force transmitted throughout the cylindrical net-like structure in the y-direction. Thus, as the cylindrical net-like structure is pulled along its axial length (x-direction), the structure will advantageously grasp a member over which it has been suitably stretched with increased force. Moreover, the greater the force applied along the axial length of the cylindrical net-like structure, the tighter the structure will grasp the enclosed member.

In the use of the present invention, the first guide ring is placed around the cervix of the expectant mother, in the pars posterior, pars lateralis and pars anterior fornices when the fetal head is engaged. As the fetal head progresses through the birth canal, the cervix will be pushed into the fornices, effectively holding the first guide ring in place. The fetal head then progresses into the tubular cylindrical net-like structure.

When the fetal head has reached the level of the symphysis pubica, the cervix is no longer pressed against the fornices and the fetal head will be fully inserted into and enveloped by the tubular cylindrical net-like structure, thereby allowing the first guide ring to move from its original position upon the application of traction to the device. Advantageously, the obstetrician can now apply traction to the device and effectively flexibly grasp and lock the fetal head into a non-traumatic net. Significant torsional and traction control is thus possible. Once the fetal head is delivered, the tubular cylindrical net-like structure is released, allowing easy access to the mouth and nares for aspiration of mucus and easy removal of meconium.

Thus, the present invention guarantees that the forces exerted on the fetus by he tubular cylindrical net-like structure are evenly distributed over a large surface area of the fetal head, unlike forces exerted by known forceps. Additionally, the present device may be utilized prior to passage of the fetal head through the birth canal thereby eliminating the difficulty of potentially traumatic forcep placement. Furthermore, insertion of the present invention into the birth canal poses a minimum amount of risk to the fetus. Advantageously, the fetus naturally and smoothly slides into the present invention, thus overcoming difficulties associated with expanding and unfolding a fan-like member around the fetus which is tightly held by the birth canal.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

More specifically, although the terms "fetus", and "fetal" are used herein, it is recognized that such terms include what may be referred to as newborn. Furthermore, the present invention is also applicable to fetuses other than human, such as animal fetuses, in which case the cylindrical net-like structure of the present invention will receive any suitable portion of the fetus, or the entire fetus. Additionally, a number of configurations and combinations of the drawstring, guide ring and introducer may be employed in the present invention.

What is claimed is:

1. An obstetric device for the tractive delivery of a fetus comprising:
   an elongated cylindrical net-like structure having a plurality of interconnected threads defining a plurality of openings;

a resilient, constrictable and expandable guide member attached at a first end of said cylindrical net-like structure for inserting said device through a birth canal and defining an opening of said net-like structure for receiving and enveloping a fetal head and guiding said cylindrical net-like structure therearound, said guide member being a ring which maintains said first end of said a net-like structure open at said opening and has a diameter at rest slightly larger than the diameter of the fetal neck; wherein said first end of said elongated net-like structure applies an increased grasping force to a fetal head inserted therein as tractive force is applied to a second end of said elongated cylindrical net-like structure.

2. The obstetric device of claim 1 wherein said plurality of interconnected threads defines a flexible fabric.

3. The obstetric device of claim 1 wherein said guide ring is mechanically expandable.

4. The obstetric device of claim 1 wherein said plurality of threads of said net-like structure are knitted to define a mesh.

5. The obstetric device of claim 1 wherein said guide ring comprises an elongated member having a first end and a second end, said elongated member being formed into a circle such that said first end is adjacent to said second end, wherein said guide ring is constrictable or expandable by the application of force thereto to constrict or enlarge said ring.

6. The obstetric device of claim 1 further comprising means for providing directional control and angular positioning of said fetal head in said birth canal.

7. The obstetric device of claim 6 wherein said means for providing directional control and angular positioning of said fetal head comprises a second guide ring attached at a second end of said cylindrical net-like structure.

8. The obstetric device of claim 1 wherein said threads are individual fibers knitted to define a mesh.

9. The obstetric device of claim 1 wherein said threads are braided strands of fibers knitted to define a mesh.

10. The obstetric device of claim 9 further comprising a drawstring attached to said first end of said cylindrical net-like structure for reducing a diameter of said first end of said cylindrical net-like structure.

11. An obstetric device for the tractive delivery of a fetus comprising:
an elongated cylindrical net-like structure having a plurality of interconnected threads defining a plurality of openings;
a resilient, constrictable and expandable guide member attached at a first end of said cylindrical net-like structure for inserting said device through a birth canal and defining an opening of said net-like structure for receiving and enveloping a fetal head and guiding said cylindrical net-like structure therearound;
wherein said first end of said elongated net-like structure applies an increased grasping force to a fetal head inserted therein as tractive force is applied to a second end of said elongated cylindrical net-like structure;
wherein said guide member comprises an inflatable annular ring.

12. The obstetric device of claim 11 wherein said inflatable annular ring comprises an expandable ring having a diameter which is expandable by introduction of a pressurized fluid so as to accommodate said fetal head.

13. The obstetric device of claim 12 wherein said inflatable ring is pneumatically or hydraulically inflatable.

14. The obstetric device of claim 12 wherein said inflatable ring is mechanically expandable.

15. The obstetric device of claim 11 further comprising handle means attached to said inflatable annular ring.

16. An obstetric device for the tractive delivery of a fetus comprising a cylindrical flexible net having a resilient, constrictable and expandable guide member located at a first opening at one end, said guide member and first opening adapted for receiving and enveloping at least a portion of a fetus within a birth canal during delivery of such fetus said guide member being a ring which maintains said one end of said flexible net open at said first opening and has a diameter at rest slightly larger than the diameter of the fetal neck said cylindrical net extending outwards from said birth canal and terminating at a second end, wherein tractive force applied to said second end tends to elongate said cylindrical flexible net to decrease the diameter of said cylindrical flexible net, thereby applying uniformly increasing forces to said fetal portion for tractive delivery of said fetus.

17. The obstetric device of claim 16 further comprising means for providing directional control and angular positioning of said fetal portion in said birth canal.

18. The obstetric device of claim 17 wherein said means for providing directional control and angular positioning of said portion of said fetus is a ring.

19. The obstetric device of claim 17 wherein said cylindrical flexible net comprises threads knitted to define a mesh.

20. The obstetric device of claim 19 wherein said threads are individual strands of fibers.

21. The obstetric device of claim 19 wherein said threads comprise braided strands of fibers.

22. The obstetric device of claim 16 further comprising a drawstring attached to said one end of said cylindrical flexible net for reducing a diameter of said first end of said net.

23. The obstetric device of claim 16 further comprising a second guide means attached to said second end of said cylindrical flexible net.

24. The obstetric device of claim 23 wherein said second guide means is a ring and provides directional control and angular positioning of said portion of said fetus.

25. An obstetric device for the tractive delivery of a fetus comprising:
an elongated, cylindrical flexible net-like structure having a plurality of interconnected threads defining a plurality of openings therein;
a first circular ring formed of a resilient member, said ring located at a first end of said net-like structure to define an opening for receiving a fetal head, wherein said ring is constrictable by the application of force to a smaller diameter for insertion into a birth canal and expandable by the application of force to a larger diameter to allow said fetal head to pass therethrough for positioning of said ring past said fetal head; and
a second circular ring attached to a second end of said net-like structure for providing directional control and angular positioning of said fetal head in said birth canal;
wherein a tractive force applied to said second end of said structure tends to elongate said net-like structure, thereby applying uniformly increasing forces to said fetal head for tractive delivery of said fetus.

* * * * *